United States Patent [19]

Kung et al.

[11] Patent Number: 4,762,915

[45] Date of Patent: Aug. 9, 1988

[54] PROTEIN-LIPOSOME CONJUGATES

[75] Inventors: Viola T. Kung, Menlo Park; Carl T. Redemann, Walnut Creek, both of Calif.

[73] Assignee: Liposome Technology, Inc., Menlo Park, Calif.

[21] Appl. No.: 692,679

[22] Filed: Jan. 18, 1985

[51] Int. Cl.$^4$ .................... A61K 39/00; A61K 9/42; A61J 5/00

[52] U.S. Cl. .................... 530/405; 530/403; 530/406; 514/2; 514/76; 424/85; 424/88; 424/450; 264/4.1

[58] Field of Search .................... 424/19, 33, 38, 85, 424/88, 94, 248.57, 250, 450; 260/112 R, 112 B; 435/7; 530/403, 405, 406; 514/2, 76; 264/4.1

[56] References Cited

U.S. PATENT DOCUMENTS 4,485,093 11/1984 Runge .................... 424/85
4,486,344 12/1984 Buckler .................... 260/121

OTHER PUBLICATIONS

Kinsky et al., *J. Imm. Meth.*, vol. 65, pp. 295–306, 1983, "An Alternative Procedure for the Preparation of Immunogenic Liposomal Model Membranes".

Kinsky et al., *Biochim. Biophys. Actu.*, vol. 769, p. 734, 1984.

Dancey et al., *J. Immunology*, vol. 122(2), Feb. 1979, "Immunogenicity of Liposomal Model Membranes Sensitized with Dinitrtophenylatedphosphatidylethanolamine Derivatives Containing Different Length Spacers".

Martin et al., *J. Biol. Chem.*, vol. 257(1), Jun. 10, 1982, "Irreversible Coupling of Immunoglobulin Fragments to Preformed Vesicles", pp. 286–288.

Huang et al., *Biochim. Biophys. Acta.*, vol. 716, 1982, pp. 140–150, "Characterization of Antibody Covalently Coupled to Liposomes".

Shen et al., *Biochim. Biophys. Acta.*, vol. 689, 1988, pp. 31–37, "An Improved Method for Covalent Attachment of Antibody to Liposomes".

*Primary Examiner*—Thomas G. Wiseman
*Assistant Examiner*—Robin Lyn Teskin
*Attorney, Agent, or Firm*—Ciotti & Murashige, Irell & Manella

[57] ABSTRACT

A lipid coupling reagent for use in coupling amine-containing molecules, such as proteins, to liposomes. The reagent includes phosphatidylethanolamine coupled to a 3–20 atom carbon-containing spacer arm terminating at a carboxyl or thiocarboxyl group. Also disclosed are liposomes prepared to include between about 1 and 20 mole percent of the coupling reagent, and liposomes containing surface arrays of proteins attached to the liposomes through the coupling reagent.

2 Claims, No Drawings

PROTEIN-LIPOSOME CONJUGATES

BACKGROUND OF THE INVENTION

1. Field of the Invention

The present invention relates to lipid coupling reagents, and in particular, to a reagent for coupling amine-containing molecules, such as protein molecules, to a lipid-surface structure, such as a liposome.

2. References

The following references are referred to herein by corresponding number:

1. Tyrell, D. A., *Biochem Biophys Acta* (1976) 457: 259.
2. Dunnick, J. K., *J Nucl Med* (1975) 16: 483.
3. Torchilin, V. P., et al, *Biochem Biophys Res Commun* (1979) 85: 1114.
4. Torchilin, V. P., *Biochem Biophys Res Commun* (1978) 85: 983.
5. Health, T. D., et al, *Biochem Biophys Acta* (1981) 640: 66.
6. Martin, et al, *Biochemistry* (1981) 26: 4229.
7. Hupfer, B., et al, *Makromol Chem* (1981) 182: 247.
8. Regen, S. L., et al, *J Am Chem Soc* (1980) 102: 6640.
9. Szoka, F. C., et al, *Ann Rev Biophys Bioeng* (1980) 9: 467.
10. Szoka, F. C., et al, *Proc Nat Acad Sci* (USA) (1978) 75: 4194.
11. Olson, F., et al, *Biochem Biophys Acta* (1979) 557: 9.
12. Dancey, G. F., et al, *J Immunol* (1979) 255: 8015.
13. Huang, A., et al, *J Biol Chem* (1980) 255: 8015.
14. U.S. Pat. No. 4,483,929 for Liposomes With Glycolipid-linked Antibodies.
15. Lowry, O. H., et al, *J Biol Chem* (1951) 193: 265.

3. Prior Art

A variety of therapeutic and diagnostic uses of liposomes have been reported. In many applications, liposomes are prepared to include surface-bound molecules such as small haptens, enzymes, antibodies, and other protein and non-protein molecules capable of conferring selected enzymatic or surface-recognition features to the liposomes. The surface molecules may function, in therapeutic applications, to target drug-containing liposomes to specific tissue or organ receptors (reference 1). In diagnostic applications of liposomes, the surface-bound molecules typically are ligands capable of binding with high affinity to analyte-related anti-ligand molecules, which may be either free in the assay reaction medium or carried on a solid surface. Binding between ligand and anti-ligand molecules leads to one of a variety of surface-attachment, agglutination, reporter-modulation or liposome-lysis events used in determining the presence and/or concentration of analyte in the reaction medium.

In some specialized uses, the surface-bound molecules may be lipid or lipid-like antigens, such as cardiolipin or glycolipid, which can be incorporated directly into the liposomes as part of the lipid components used in forming liposomes. In the more typical case, the molecules are relatively water-soluble antigens or proteins, which are preferably covalently attached to surface lipid components in the liposomes.

Several methods for coupling soluble molecules, such as proteins, to lipid structures, such as liposomes, have been reported. Some of these methods involve direct coupling of proteins to unmodified surface lipids by water-soluble cross-linking agents such as 1-ethyl,3-(3-dimethylaminopropyl)carbodiimide(EDCI) (reference 2), glutaraldehyde (reference 3), or suberimidate (reference 4). Cross-linking methods of this type have not been entirely satisfactory in that significant cross-linking of vesicles, or proteins or both may occur. The extent of specific ligand binding achievable is also generally quite low.

One protein coupling technique which allows relatively high levels of protein binding to liposomes has been described by Heath, et al (reference 5). The method involves periodate oxidation of glycosphingolipids in the liposome outer membranes, to form reactive surface aldehyde groups. Proteins are then attached to the aldehyde groups through Schiff-base formation, followed by reduction with $NaBH_4$ or reductive amination with $NaBH_3CN$. Under optimal conditions, up to about 20% of the protein may be coupled to the oxidized vesicles, and coupling ratios between 100–200 $\mu$g protein (IgG) per $\mu$mole lipid may be achieved. One limitation of the method is the requirement for glycosphingolipids in the liposomes. General oxidative damage to liposomes caused by periodate oxidation, and the need to remove periodate before protein coupling is carried out, are other limitations.

A second protein coupling method which has been shown to produce high coupling ratios is disclosed in U.S. Pat. No. 4,429,008 to Martin, et al. The liposomes in this method are formed by incorporating a thiol-reactive lipid, such as (N-[4-(p-maleimidophenyl)butyryl]-phosphatidylethanolamine (MPB-PE) or (N-[3-(pyridyl-2-dithiopropionyl]phosphatidylethanolamine) (PDP-PE). The thiol-reactive liposomes are reacted with a protein bearing a free sulfhydryl group, or with one which has been thiolated to produce such a group, under conditions which lead to disulfide or thioether coupling to the thiol-reactive surface lipid. Coupling efficiencies of between 15%–30%, and coupling ratios greater than about 200 $\mu$g protein (IgG)/$\mu$mole lipid have been obtained (reference 6). The method is limited to proteins which have an available free sulfhydryl group or which can be thiolated without loss of protein activity.

SUMMARY OF THE INVENTION

It is a general object of the present invention to provide a novel liposome/binding molecule coupling reagent and method which substantially overcomes problems and limitations associated with the prior art.

A more specific object of the invention is to provide such a reagent and method which can be used to produce protein coupling efficiencies of up to about 60% and coupling ratios of about 300 $\mu$g protein/$\mu$mole lipid or greater.

Another object of the invention is to provide such a reagent and method which do not require special reactive groups, such as free sulfhydryl groups, for coupling.

It is another object of the invention to provide such a coupling reagent which is easily prepared and stable either in free form or when incorporated into liposomes.

Still another object of the invention is to provide in such a reagent, a spacer arm whose length can be tailored readily according to reagent preparation techniques, to achieve optimal coupling ratios and efficiencies.

The invention includes a lipid coupling reagent for use in coupling amine-containing molecules, such as proteins, to lipid-surface structures, such as liposomes. The reagent includes a carboxylated or thiocarboxylated derivative of a lipid amine, and having the general formula

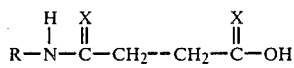

where R—NH$_2$ is a lipid amine, X is oxygen (O) or sulfur (S) and CH$_2$ - - - CH$_2$ is a linear carbon-containing chain having a total chain length between 3 and about 20 atoms. In one preferred embodiment of the invention, the reagent takes the form

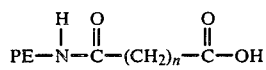

where n=6-14, and PE is phosphatidylethanolamine.

The carboxylated reagent is formed, in accordance with the method of the invention, by reacting R—NH$_2$ with an anhydride of a dicarboxylic acid in the presence of a tertiary amine. Protein coupling to liposomes containing the reagent is carried out in an aqueous medium in the presence of a soluble carboxyl/amine linking agent.

The invention further includes liposomes containing the reagent, at a concentration preferably between 1 and 20 mole percent, and liposomes having surface arrays of amine-containing molecules, such as proteins, coupled to the liposomes through the reagent.

These and other objects and features of the present invention will become more fully apparent from the following detailed description of the invention, when read in conjunction with the accompanying drawings.

BRIEF DESCRIPTION OF THE DRAWINGS

FIGS. 1-3 show steps in the synthesis of the carboxylated PE reagent of the invention; and FIG. 4 shows a coupling reaction for attaching a protein to the reagent, with such carried in a liposome.

DETAILED DESCRIPTION OF THE INVENTION

1. Preparing the Lipid Coupling Reagent

The lipid PE coupling reagent of the invention has the general formula

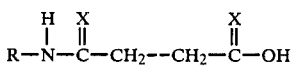

where R—NH$_2$ is a lipid amine, X is oxygen (O) or sulfur (S) and CH$_2$ - - - CH$_2$ is an amide-linked carbon-containing chain having a chain length of between 3 and up to about 20 atoms. The lipid amine of the reagent serves to anchor the reagent in an ordered lipid layer of a lipid-surface structure, such as the outer phospholipid layer of a liposome. The lipid amine may include any natural or synthetic lipid having a terminal amine and whose lipid moiety can function to anchor the reagent in such ordered lipid layer, with the amide-linked chain moiety being held in the outer polar surface region surrounding the lipid layer. Lipid amines suitable in a reagent having a relatively short and/or hydrophilic amide-linked chain include fatty acyl amines, sterol amines, and natural or synthetic phospholipid amines, such as phosphatidylethanolamine (PE). In a reagent having a longer, hydrophobic chain, PE is the preferred lipid amine. Sources of and methods for synthesizing natural and synthetic lipid amines of the type just mentioned are well known. In particular, purified and partially purified PE preparations are commercially available, or may be prepared by known methods, and these may be purified and/or modified in acyl chain composition according to known techniques.

The amide-linked chain moiety, also referred to herein as a spacer arm, acts to place the terminal acid group of the reagent at a position which is favorable for end group coupling, when the reagent is anchored in a surface bilayer, as will be described below. The CH$_2$ - - - CH$_2$ chain in the spacer arm moiety generally includes a carbon-containing linear chain having various degrees of saturation and/or heteroatom compositions. One preferred type of chain is a simple saturated acyl chain of the form (CH$_2$)$_n$, where n=3-20. The carbon atoms in the chain may also be partially unsaturated, including either ethylenic or ethylynic bonds, and/or may include such heteroatoms as carbon-linked O, S or nitrogen (N) atoms, forming ester, ether, thioester, thioether, amide or amine linkages within the chain. The chain atoms themselves may be substituted with carbon, hydrogen, O, S, or N atoms, or groups containing these atoms such as short chain acyl groups or the like. Examples I-IV describe carboxylated PE reagents having various-length saturated acyl chain spacer arms. Example V describes a carboxylated PE reagent having as a spacer arm, a disuccinoylethylenediamine (DES) moiety of the form

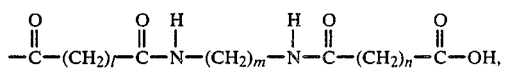

where l, m, n=2; more generally, l+m+n=1-10. Another general type of spacer arm includes a polypeptide chain composed of preferably between about 2-7 amino acids.

A preferred method of forming the coupling reagent of the invention is outlined generally in FIGS. 1-3. The method illustrated is applicable particularly to forming the PE amide carboxylic acid reagent shown in FIG. 3. Analogous methods can be used to form carboxylic acid derivatives of other lipid amines, or thiocarboxylic acid lipid amide derivatives. The method involves first providing a dicarboxylic anhydride of the form

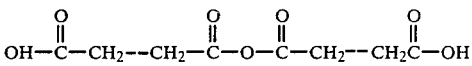

where CH$_2$ - - - CH$_2$ has the chain characteristics noted above. For some selected chains, the anhydride may be obtained commercially, such as illustrated in Example II where succinic anhydride is used. Where the anhydride is not commercially available, it may be prepared, typically from the dicarboxylic acid of the anhydride. The dicarboxylic acid may be obtained commercially, as in Examples I, III, and IV, or prepared from more basic starting materials, as in Example V.

FIG. 1 below illustrates a preferred method for preparing a selected anhydride. As seen, 2 mole equivalents of the corresponding dicarboxylic acid of the form

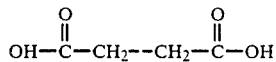

are reacted with 1 mole equivalent of a carbodiimide coupling reagent. Dicyclohexylcarbodiimide (DCDI) is suitable for use in organic solvents, such as methylene chloride, which are typically used. The reaction is carried out preferably under a non-oxidizing atmosphere, such as nitrogen, for a period of up to several days, at a temperature normally between about 10° and 25° C. The dicyclohexylurea formed in the reaction need not be removed from the anhydride reaction product before further coupling the anhydride to PE.

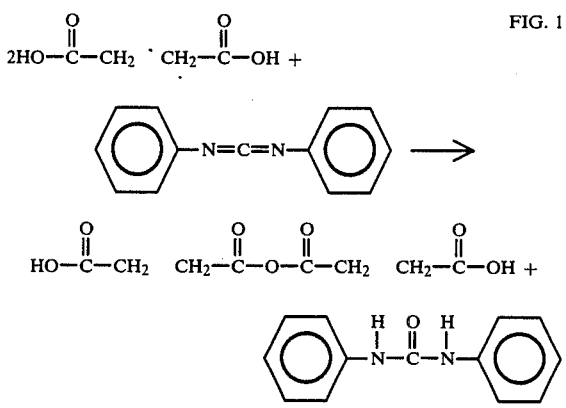

FIG. 1

In the second step of the method, illustrated in FIG. 2, 1 mole equivalent of the anhydride is reacted with about 1 mole equivalent of PE in the presence of about 3 mole equivalents of a tertiary amine, such as triethylamine. The reaction is typically prepared by adding a solution of PE and the tertiary amine in an organic solvent which is miscible with the solvent used in the anhydride-forming reaction. The reaction is carried out preferably under a non-oxidizing atmosphere for a period of up to several days, also at a temperature of between about 10° and 24°. As seen in FIG. 2, the resulting product is a tertiary amine salt of the PE-amide of dicarboxylic acid.

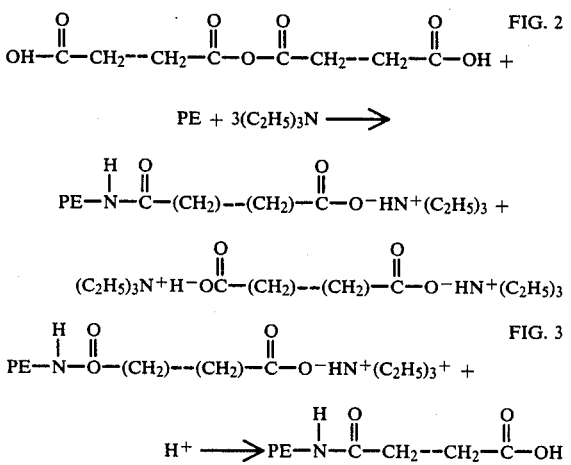

FIG. 2

FIG. 3

The reaction mixture is then washed with an acidified aqueous solution to form the PE-amine carboxylic acid reagent which is shown in the second line of FIG. 3. After removing the aqueous phase, the organic phase mixture may be dried, for example, over anhydrous sodium sulfate.

The carboxylated PE reagent is purified by conventional chromatographic techniques, such as silica gel column chromatography, using a selected solvent system to elute the reagent. The eluate fractions can be monitored conventionally by thin-layer chromatography (TLC). Examples I, II, III, and IV detail the preparation and purification of the PE-amides of glutaric acid, succinic acid, 1,12-dodecanedicarboxylic and 1,20-eicosanedicarboxylic acid, respectively. Example V describes the preparation and purification of the PE amide of DES.

2. Coupling Surface Molecules to Lipid Bodies

The reagent of the invention is useful in coupling amine-containing molecules to the surfaces of lipid-surface structures. The amine-containing molecules, which are also referred to herein as surface molecules, are selected generally from any water-soluble molecule or multi-unit aggregate which contains one or more amine groups which are accessible for reacting with the reagent, under selected coupling conditions, to form a stable amide linkage between the reagent and the molecule. Exemplary surface molecules include non-polypeptide haptens, polypeptides, proteins, particularly antibody or antibody fragment molecules and enzymes, nucleic acid strands, amine-containing sugars, and molecules which have been modified, by conventional chemical modification techniques, to contain accessible amine groups. Representative classes of enzymes contemplated herein include oxidoreductases, typified by luciferase, glucose oxidase, galactose oxidase and catalase; hydrolases, typified by various types of phosphatases; glycoside hydrolases, such as $\beta$-galactosidase; peptidases; and lyases. Representative classes of antibodies include IgG, IgM, IgE, IgA, and IgD molecules and the Fab[1] and F(ab)[2] fragments thereof. Further, two or more different surface molecules, such as an enzyme and an antibody, may be coupled to the same lipid structure surface, either in successive coupling reactions or a single reaction where the reaction mixture contains a selected ratio of both types of molecules. The invention will be described with particular reference to coupling water-soluble proteins, and especially antibody molecules, to liposomes incorporating the reagent.

The lipid-surface structures generally include various types of macromolecular particles having an ordered lipid outer layer and typically a phospholipid layer which has an internal hydrophobic region and a surface polar head-group region. The structures may take the form of closed unilamellar or multilamellar bilayer vesicles encapsulating an aqueous interior region, such vesicles being referred to herein as liposomes. Amorphous lipid bilayer structures, including ribbon-like bodies and small aggregates of vesicles or floculents are also contemplated. Other possible lipid-surface structures formed by encapsulating an emulsified oil droplet with a lipid monolayer, such as a phospholipid monolayer, are also suitable. The lipid components making up the ordered lipid layer may be freely mobile in the plane of the layer, or may be partially immobilized by lipid-lipid polymerization, according to lipid monolayer polymerization reactions described, for example, in above references 7 and 8.

In one method for coupling surface molecules to lipid-surface structures, the structures are prepared to include a surface array of the lipid coupling reagent, typically at a surface concentration of between about 1 and 10 mole percent with respect to surface lipid components in the outer surface lipid layer. Such structures can be readily formed by including the reagent in the lipid mixture used in preparing the lipid structures, at the selected mole percent. The coupling method of the invention will be described below with respect to liposomal structures, it being understood that analogous coupling methods are applicable to other types of lipid-surface structures, including lipid monolayers.

To prepare liposomes containing a surface array of the reagent, the liposome lipids are mixed with a selected mole percent of the reagent, then formed according to conventional liposome preparation methods. Properties of and methods for preparing liposomes have been detailed in the literature, and the reader is referred particularly to above references 9 and 10, and references cited therein, for a comprehensive discussion of the topic. Liposomes for use in the present invention are preferably composed of between about 40-90% phospholipid—typically phosphatidylcholine (PC) and phosphatidylglycerol (PG)—between about 10-50 mole percent cholesterol, and between about 1 and 20 mole percent of the coupling reagent, although a higher mole ratio of reagent may be used if the total negative surface charge due to the charged carboxyl groups does not adversely affect the coupling and/or end-use binding reaction on the liposome surface. One preferred liposome composition, described in Example VI, contains 40 mole percent PC, 50 mole percent cholesterol, and 10 mole percent coupling reagent. The liposomes, once formed, may be sized, for example, by extrusion through a micropore membrane and/or washed by known techniques (reference 11). The liposomes may be suspended to a final concentration of between about 1-5 micromoles lipid/ml in a suitable activation buffer, such as phosphate buffer, pH 5.0, containing 0.1 to 0.2M NaCl.

The reagent-containing liposomes are activated, for coupling to surface molecules, by addition of a water-soluble carboxyl/amine linking agent to the liposome suspension from above. The linking agent is one which is capable of reacting with a carboxyl or thiocarboxyl group, to form an activated complex which is reactive toward amine groups, to form a stable amide or thioamide linkage. Exemplary linking agents include carbodiimides, preferably water soluble carbodiimides such as 1-ethyl-3-(3-dimethylaminopropyl)-carbodiimide (EDCl) and imidazoles, such as N-hydroxy imidazole. The linking is added to a final concentration of between about 1-2 mole equivalents per mole of coupling reagent in the suspension. The activation reaction is carried out usually for about 1 hr at room temperature. The activated liposome complex which is formed is illustrated in the upper line of FIG. 4, where the linking agent is a carbodiimide, such as EDCl. The complex need not be separated from unreacted linking agent before further coupling to the surface molecules.

To couple surface molecules to the activated liposomes, the activated liposome suspension is mixed with an aqueous solution of the binding molecules, and the mixture is allowed to react under conditions which lead to amide-bond formation between the activated reagent and the molecules, as shown in the lower line of FIG. 4. The coupling reaction medium is preferably adjusted to a pH of about 7-9, and to a salt concentration of between about 0.1 and 0.2M. The reaction is carried out normally between about 4° and 10° C., until a maximum ratio of surface binding has occurred. Overnight reaction times are normal. The reaction may be quenched by the addition of a suitable amine-containing compound, such as an amino acid.

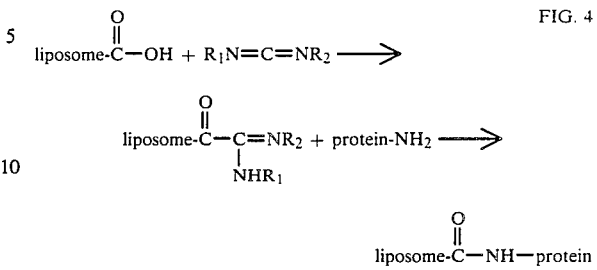

FIG. 4

The liposomes and surface-bound molecules are separated from the non-lipid-associated molecules in the reaction mixture by conventional separation techniques, such as molecular-sieve chromatography or centrifugation, for example, through a metrizamide density gradient. The liposomes may be further washed to remove non-specifically bound surface molecules. Example VII details methods of the coupling IgG molecules to each of the four liposome suspensions prepared in Examples I-IV.

The final surface concentration of bound molecules can be adjusted by varying the initial ratio of added binding molecules to liposome lipid. Optimal surface concentrations of bound protein molecules are achieved at initial protein/lipid concentration ratios of about 0.5 to 2.0 mg protein/$\mu$mole lipid. In each of the coupling methods described in Example VII, about 0.75 mg IgG was reacted with about 1.5 $\mu$mole liposome lipid.

According to an important feature of the invention, the efficiency and extent of coupling are both quite high at spacer arm chain lengths between 3 and about 20 atoms. At a chain length of 2 or less, i.e., for $CH_2$—$CH_2$ and $CH_2$ "chains," very low efficiencies and coupling ratios are observed. At chain lengths greater than about 20 atoms, the reagent may be difficult to synthesize, due in part to a general lack of commercial availability of long-chain dicarboxylic acids. Further, chains having lengths of about 20 atoms show reduced ratios of specific to control (non-specific) protein coupling. As will be seen from data presented in Example VII, the several reagents formed with saturated hydrocarbon spacer arm chains with lengths from 3-20 atoms all showed coupling efficiencies of at least about 30% and coupling ratios, for IgG, of greater than about 150 $\mu$g proteins/$\mu$mole liposome lipid. At an optimal $CH_2$---$CH_2$ chain length of 12, the coupling efficiency was about 60% and the coupling ratio, about 300 $\mu$g IgG/$\mu$mole lipid. This result is surprising in view of the expected tendency of long-chain acyl groups, such as a 12-atom chain to partition in the surface bilayer. For example, studies by others on the immunogenicity of liposomes sensitized with dinitrophenyphosphate-derivatized PE containing different-length spacers show highest activity at chain lengths about 3 or 4 atoms and a sharp dropoff in immunogenic activity at chain lengths about 7-10 atoms. (reference 12).

An optimal chain length of about 12 atoms for an acyl chain spacer arm has been shown. The optimal chain length may vary according to the solubility and charge characteristics of the spacer arm chain as can be readily determined from preliminary coupling-reaction studies.

In an alternative coupling method, the reagent is first reacted with surface molecules in the presence of a suitable linking agent under coupling conditions described above, to form a surface molecule/lipid reagent conjugate. The conjugate-forming reaction is preferably carried out in the presence of a low concentration of detergent, such as deoxycholate or octalglucoside, to promote dispersion of the lipid reagent in solution. The conjugate is then added to a suspension of liposomes (or other lipid-surface structure), formed in accordance with the general procedures outlined above, under conditions which allow diffusion of the lipid moiety of the conjugate into the outer surfaces of the liposomes. The diffusion reaction likely involves lipid exchange between a micellar or other ordered lipid state of the conjugate and the liposome bilayer membrane. The diffusion reaction, like the coupling reaction, is normally carried out in a low concentration of detergent to accelerate the exchange reaction. The lipid conjugate is added to the liposomes in an amount selected to achieve a desired surface concentration of surface molecules on the liposome particles. After an incubation period of up to several hours, the liposomes are separated from the detergent and unbound conjugate molecules by centrifugation, molecular-sieve chromatography or other separation method. The reader is referred to references 13 and 14 for a discussion of procedures and conditions suitable for forming lipid/protein conjugates and for diffusing such conjugates into liposomes.

Several liposome assays using liposome reagents prepared by the method of the invention were studied to demonstrate the use of the method in coupling surface-binding molecules to liposomes. The first assay was designed to show coupling of a relatively large protein antigen, bovine serum albumin (BSA), to large liposomes, and agglutination of the BSA-carrying liposomes by anti-BSA antibody. The liposomes were formed of phosphatidylcholine (PC):cholesterol:PE amide of glutaric acid, in a ratio of 20:8:2, and prepared to include encapsulated erioglaucine (a water-soluble blue dye). The BSA was reacted with activated liposomes at a ratio of about 0.5 mg protein/μmole lipid. The protein coupling ratio was about 90 μg protein/μmole lipid. Large-liposome agglutination assays were performed according to the general method described in co-owned patent application for "Large-Liposome Agglutination Reagent and Method", Ser. No. 517,826, filed July 27, 1983. In a typical assay, 50 nmole of liposomes showed strong agglutination with 14 μg rabbit anti-DNP BSA (obtained from Miles Labs, Elkhart, IN). No non-specific agglutination was seen with human IgG or rabbit anti-human IgM.

A similar type of large-liposome agglutination assay was designed to show coupling of a nuclear antigen material to liposomes and agglutination of the liposomes by anti-nuclear antibodies (ANA). Large liposomes prepared to include PC:cholesterol:PE amide of glutaric acid:PE-rhodamine (a lipid-soluble pink dye) at a ratio of 20:8:2:0.078 were prepared as in the just-cited co-owned patent application. Calf thymus antigen, a mixture of macromolecular antigens derived from thymus nuclei, including DNA, DNA-histone complex, histones, ribonucleaoprotein, and RNA, were reacted with activated liposomes at a ratio of about 0.075 mg antigen protein per μmole liposomes. In large-liposome agglutination assays performed as above, liposomes were agglutinated by positive ANA serum, but not negative serum.

A third type of assay was based on liposome-enhanced agglutination, as described generally in the co-owned patent application for "Enhanced Agglutination Method and Kit", Ser. No. 486,793, filed Apr. 20, 1983. Liposomes composed of PC:PG:cholesterol:PE amide of glutaric acid, at a ratio of 7:2:10:1 were prepared by a reverse evaporation procedure described in the just-cited application. Lens culinaris protein, a sugar-binding lectin protein, was reacted with the activated liposomes, at a ratio of about 0.8 mg protein per 1.6 μmole liposome lipid. The coupling ratio was about 260 μg protein per μmole lipid. The liposome reagent was reacted, in a latex agglutination assay test for rheumatoid factor (an IgM antibody) containing positive rheumatoid factor serum and a latex agglutination reagent composed of latex having surface-bound, heat-denatured IgG. In this assay, the normal agglutination of the latex by cross-linking with rheumatoid factor analyte is enhanced by the presence of liposome-bound lens culinaris lectin, which binds to IgM antibodies. The lens culinaris liposome reagent enhanced latex agglutination specifically in the presence of rheumatoid factor, as anticipated.

A final assay procedure involved ligand-specific binding of an anti-ligand reporter conjugate to liposomes having ligand molecules coupled to the liposome surfaces by the method of the invention. Large liposomes composed of PC:cholesterol:PE amide of glutaric acid, at a ratio of 20:8:4, were prepared by a reverse evaporation method, to contain encapsulated erioglaucine. The activated liposomes were reacted with mouse monoclonal antibody against hepatitis B surface antigen (HBsAg), at a ratio of about 0.3 mg antibody per μmole liposome lipid. In a first binding study the liposomes were incubated with fluorescein-labeled rabbit antibody against mouse IgG. After reacting the antibody and liposomes, the unbound antibody was removed by centrifugation and the liposomes were viewed under a fluorescence microscope. A readily detectable fluorescence intensity was observed. This study demonstrates that the antigenic sites of the anti-HBsAg antibody were not destroyed by the coupling reaction. In a second method, aliquots of the liposomes were incubated with increasing amounts of horseradish peroxidase-labeled HBsAg antigen. After removing unbound material by centrifugation, and resuspending the liposomes in a suitable assay buffer, the enzyme activity was measured. The peroxidase-labeled antigen could be detected at a sensitivity level of about 20 μg enzyme-labeled antigen. The second test indicates that the antigen-binding activity of the anti-HBsAg antibody was not destroyed in the coupling reaction.

From the foregoing, it can be appreciated how various objects and features of the invention are met. The coupling reagent of the invention can be easily formed to include one of a number of different chains having selected lengths and atom compositions. Where the dicarboxylic acid precursor of the spacer arm in the reagent is available, the reagent can be formed by a simple two-step procedure which requires no intermediate separation or product-isolation step.

The reagent is stable, and can be stored for extended periods in free form or incorporated into the lipid layer(s) of lipid-surface structures, such as the bilayers of liposomes.

The reagent allows the coupling of large soluble proteins to lipid body surfaces, such as liposomes, at efficiencies up to 60% and at coupling ratios of up to about 300 μg protein per μmole ml. The best coupling efficiency achieveable with the reagent of the invention is about twice that of the most efficient coupling reagents known in the prior art, and the best coupling ratios are comparable to the best coupling methods currently available. The coupling method does not inactivate surface molecules being attached to the lipid surfaces, as evidenced by the retention of both antigenic and antigen-binding activity of a number of types of surface molecules coupled to liposomes.

The PE-reagent can be included in liposomes and similar lipid-surface structures, up to 20 mole percent or more, without significantly affecting desired membrane properties, since PE is itself a common lipid in natural and artificial bilayer membranes.

Finally, the coupling reaction is not restricted to proteins having free sulfhydryl groups or the like, and is therefore applicable to a wide range of binding molecules.

The following examples are intended to illustrate the method and reagent of the invention, but in no way to limit the scope thereof.

EXAMPLE I

Preparing the PE Amide of Glutaric Acid

Glutaric acid was obtained from Aldrich Chemical Co. (Milwaukee, WI); dicyclohexyl carbodiimide (DCDI) from Aldrich Chemical Co. (Milwaukee, WI); PE from Avanti Polar Lipids (Birmingham, AL); and triethylamine from Pierce Chemical (Rockford, IL). Silica gel (E. M. Kieselgel 60, 70–230 mesh) was obtained from Van Waters & Rogers (San Francisco, CA), and thin-layer chromatography (TLC) silica gel plates were obtained from J. T. Baker (Phillipsburg, NJ).

To form the anhydride of glutaric acid, 10.6 mg of glutaric acid (0.080 mmoles) and 8.7 mg DCDI (0.042 mmoles) were combined in 2 ml methylene chloride in a screw-cap tube. The tube was capped and the mixture stirred under nitrogen at 23° C. for 48 hours with a magnetic stirring flea.

A solution of PE (0.038 mmoles) in 2 ml chloroform and 15 µl of triethylamine (0.108 mmoles) were added to the glutaric anhydride/DCDI solution. The reaction mixture was sealed under nitrogen atmosphere and allowed to react at 23° C. for three days. Following this, the mixture was acidified by adding 5 ml chloroform and 4 ml 0.02M phosphate/0.02M citrate buffer, pH 5.5, with vigorous shaking. The aqueous phase was separated by low speed centrifigation and discarded. The organic phase was dried over anhydrous sodium sulfate.

The desired N-glutaryl PE was purified by silica gel column chromatography. The dried chloroform solution was introduced into a 1 cm×20 cm silica gel (Kieselgel 60) column and fractions eluted by passing through the column 50 ml chloroform effluent solutions containing successively, 0%, 10%, 20%, 30%, and 50% methanol. The fractions eluted at each of the five different methanol concentrations were analyzed by TLC on silica gel plates developed with chloroform:methanol:-water (65:25:4 v/v/v). The presence of N-glutaryl PE (PE amide of gluatic acid) was detected by $I_2$ vapor absorption. N-glutaryl PE had an $R_f$ value of about 0.3.

Most of the product reagent was found in the 30% methanol effluent. Evaporation of the effluent fractions containing only the product reagent yielded 26.8 mg of a colorless wax when dried to a constant weight under high vacuum. The calculated phosphorus in N-glutaryl PE is 3.60%. The actual phosphorus measured was 4.01%.

EXAMPLE II

Preparation of PE Amide of Succinic Acid

Succinic anhydride was obtained from Aldrich Chemical Co. (Milwaukee, WI). A mixture containing 0.03 mmoles of PE, 4.4 mg succinic anhydride (0.04 mmoles) and 10 µl of triethylamine (0.072 mmoles) in 2 ml chloroform was prepared in a screw-capped tube. The mixture was stirred under nitrogen for 24 hours at 23° C.

The reaction mixture was washed and acidified, as in Example I, and the resulting washed choloroform solution was chromatographed on a silica gel column as above. The column material was eluted, successively, with 50 ml chloroform solutions containing 0%, 10%, 20%, 25%, and 30% methanol. The eluates were monitored by TLC as in Example I. The desired N-succinyl PE (PE amide of succinic acid) showed an $R_f$ value of about 0.26.

The bulk of the desired reagent eluted in the last part of the 25% methanol in chloroform effluent, and in the first part of the 30% methanol effluent. Fractions containing only the desired product, as monitored by TLC, were dried under vacuum yielding a colorless wax whose weight was near the total theoretical yield of 32 mg.

EXAMPLE III

Preparation of PE Amide of 1,12-Dodecanedicarboxylic Acid 1,12-dodecanedicarboxylic acid was obtained from Aldrich Chemical Co. (Milwaukee, WI). The anhydride of the acid was formed by reaction with DCDI in 2 ml methylene chloride, as described in Example I. To the resulting anhydride/DCDI solution were added 2 ml of chloroform solution of 0.03 mmole PE and 15 µl triethylamine. The mixture was stirred under a nitrogen atmosphere for 24 hours at 23° C., and washed and acidified as in Example I.

The washed chloroform solution was chromatographed on a silica gel column as in Example I, using 50 ml solution volumns of chloroform containing, successively, 0%, 10%, 20%, 25%, or 30% methanol. The effluent fractions were monitored by TLC as in Example I. The desired PE amide of 1-12-dodecanedicarboxylic acid showed an $R_f$ value of about 0.60. This $R_f$ value is about the same as PE in the chloroform:methanol:$H_2O$ (65:25:4 v/v/v) developing solvent, but can be distinguished from PE by the absence of a color reaction when exposed to a ninhydrin spraying reagent. The desired compound eluted primarily in the late 25% and 30% methanol effluent solution. The fractions containing only the desired compound were combined and dried under vacuum, giving a colorless wax at an approximate yield of 42% of theoretical yield.

EXAMPLE IV

Preparing PE Amide of 1,20-Eicosanedicarboxylic Acid 1,20-eicosanedicarboxylic acid was obtained from Pfalz & Bauer (Stamford, CT). The anhydride of 1,20-eicosanedicarboxylic acid was formed as in Example I, and reacted with a chloroform solution PE and triethylamine, also in accordance with this example, to form the PE amide of the eicosanedicarboxylic acid. The chloroform solution was washed and acidified as in the above examples, and chromatographed on a silica gel column using 50 ml chloroform effluent solutions containing successively 0%, 10%, 15%, 20%, 30%, 50% methanol to elute the desired PE amide carboxylic acid reagent. The eluate fractions were analyzed by silica gel TLC, on which the reagent showed an $R_f$ value of about 0.51 with the solvent system described in the examples above.

The fractions containing only the PE amide reagent were combined and dried under vacuum, yielding a colorless wax at a yield of about 40% of the theoretical yield. The calculated phosphorus was 2.8%; the actual phosphorus measured was 3.1%.

EXAMPLE V

Preparing the PE Amide of Disuccinoylethylenediamine

Ethylenediamine was obtained from Aldrich Chemical (Milwaukee, WI); N-hydroxy-succinimide from Aldrich Chemical (Milwaukee, WI); and tetrahydrofuran from Aldrich Chemical (Milwaukee, WI).

Disuccinoylethylenediamine (DES) was formed by reacting 2 gm succinic anhydride (Example II) (0.02 moles) with 0.6 gm ethylenediamine (0.01 mole) and 2 gm triethylamine in 45 ml methylene chloride:tetrahydrofuran (1:1 v/v). The reaction mixture was stirred for one hour at room temperature.

Following removal of the solvent under reduced pressure, the residue was acidified to pH 3.0 with the dilute HCl, causing a colorless solid to aggregate. Crystalization from 25 ml hot water, followed by cooling to 4° C., yielded 1.18 gram of colorless crystals which melted at 205° C.

The anhydride of DES was formed as in Example I, by reacting DES (a dicarboxylic acid) with about 0.5 mole equivalents of DCDI in methylene chloride under a nitrogen atmosphere.

To form the PE amide of DES, about 63 mg of the anhydride of DES from above (about 0.125 mmoles dissolved in 0.5 ml methylene chloride), was added to 2.1 ml chloroform containing 42.2 mg PE (0.05 mmoles) and 15 μl of triethylamine. The reaction mixture was permitted to stand for 18 hr at room temperature. The reacted mixture was washed and chromatographed by silica gel chromatography, also as described above, to give a colorless oil identified as the desired product.

EXAMPLE VI

Preparing Liposomes Containing PE Amide Dicarboxylic Acids

The PE-amide of 1,8-octanedicarboxylic was prepared according to the general procedures of Examples I–IV. Large, oligolamellar vesicle suspensions, each containing one of the four PE amide dicarboxylic acid reagents from Examples I–IV or the PE amide of 1,8-octanedicarboxylic acid, were prepared by a reverse evaporation phase method described generally in reference 9. For each suspension, cholesterol (10 μmoles), PC (9 μmoles) and a selected PE amide reagent (1 μmole) were dissolved in 1 ml of diethyl ether. To this was added 325 μl of 10 mM $NaPO_4$, 0.15 NaCl (pH 5.0), and the two phases were emulsified by sonication for one min at 25° C. in a bath sonicator. Ether was removed under reduced pressure at room temperature. The resulting gel was agitated by vortexing in 10 mM phosphate buffer, pH 5.0, containing 0.15M NaCl, to a final concentration of between about 1–2 μmole lipid/ml.

EXAMPLE VII

Coupling IgG to Carboxylated PE Liposome Suspensions 1-ethyl-3-(3-dimethylaminopropyl)-carbodiimide (EDCl) was obtained from Pierce Chemical Co. (Rockford, IL). Mouse IgG was obtained from Cappel Labs (Malvern, PA). Each of the five liposomal suspensions (1.5 μmole) from Example VI was mixed with EDCI (4 mg) in 1.5 ml of 10 mM $NaPO_4$, 0.15M NaCl, pH 5.0. The reaction was carried out at room temperature for one hr.

The liposome/EDCI mixture (1.5 ml) was mixed with 75 μl of mouse IgG (10 mg/ml) and 75 μl of 1M NaCl, and the coupling-reaction mixture adjusted to pH 8.0. Each reaction was carried out overnight at 4° C. Unreacted protein was separated from liposome-conjugated protein by metrizamide density gradient centrifugation, according to a standard procedure. Control coupling reactions were performed by substituting buffer for ECDI.

The amount of protein bound to the liposomes was determined by the Lowry protein assay described in reference 15. The concentration of liposomal lipid was determined from $I^{125}$ radioactivity levels, based on a known amount of PE-$I^{125}$ included in the liposome preparations. Based on the measured protein and lipid concentrations, the protein to lipid coupling ratios, expressed in micrograms protein/μmole, lipid were determined. The values obtained are shown in Table I below, for each of the four different liposomal suspensions which were examined.

The coupling efficiencies, also shown in Table I, were calculated as the ratio of liposome-bound protein to total protein added to the reaction mixture.

TABLE I

| Sample | Protein (μg)/Lipid (μmole) | | Coupling Efficiency (%) |
| --- | --- | --- | --- |
| | Control | +EDCI | |
| PE—N—C—$(CH_2)_n$—C—OH (with two C=O) | | | |
| n = 3 | 6 | 149 | 30 |
| 5 | 13 | 142 | 30 |
| 8 | 34 | 197 | 40 |
| 12 | 20 | 290 | 60 |
| 20 | 164 | 313 | 60 |

As seen, all five PE dicarboxylic acid reagents showed high coupling efficiencies and relatively high levels of protein coupling. The optimal coupling ratio, relative to control values, occurred at n=12. Although the n=20 reagent gave high coupling values, control values were also substantially higher than for the four shorter-arm reagents.

While the invention has been described in preferred embodiments and illustrated with specific examples, it will be appreciated that various changes and modifications can be made without departing from the invention.

It is claimed:

1. A method of attaching protein molecules to liposomes at a concentration of at least about 150 μg protein per μmole lipid, comprising providing a carboxylated lipid coupling reagent of the form $$PE-\underset{H}{N}-\underset{O}{C}-CH_2---CH_2-\underset{O}{C}-OH$$

where PE—NH$_2$ is phosphatidylethanolamine and CH$_2$ - - - CH$_2$ is a carbon-containing chain having a total chain length between 3 and about 20 atoms preparing liposomes containing between about 1 and 20 mole percent of the coupling reagent, activating the liposomes with a water-soluble carbodiimide, and reacting the activated liposomes with such protein, at a protein concentration of at least about 300–500 μg/μmole liposome lipid.

2. The method of claim 1, wherein CH$_2$ - - - CH$_2$ is a hydrocarbon chain between about 8 and 12 carbons long.

* * * * *